US006545194B1

(12) United States Patent
Schmidt et al.

(10) Patent No.: US 6,545,194 B1
(45) Date of Patent: Apr. 8, 2003

(54) DEVICE FOR MANAGING BODY FLUIDS COMPRISING A FAST ACQUIRING LIQUID HANDLING MEMBER THAT EXPANDS UPON LIQUID ACQUISITION AND CONTRACTS UPON LIQUID RELEASE

(75) Inventors: Mattias Schmidt, Idstein (DE); Bruno Johannes Ehrnsperger, Frankfurt (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/720,191

(22) PCT Filed: Jun. 29, 1999

(86) PCT No.: PCT/US99/14641

§ 371 (c)(1),
(2), (4) Date: Dec. 20, 2000

(87) PCT Pub. No.: WO00/00139

PCT Pub. Date: Jan. 6, 2000

Related U.S. Application Data

(63) Continuation-in-part of application No. 09/646,076, filed on Sep. 13, 2000.

(30) Foreign Application Priority Data

Jun. 29, 1998 (WO) .............................. PCT/US98/13449
Jun. 29, 1998 (WO) .............................. PCT/US98/13497
Jun. 29, 1998 (WO) .............................. PCT/US98/13521
Jun. 29, 1998 (WO) .............................. PCT/US98/13523

(51) Int. Cl.$^7$ .............................................. A61F 13/15
(52) U.S. Cl. ..................................................... 604/367
(58) Field of Search .......................... 604/385.01, 378, 604/367

(56) References Cited

U.S. PATENT DOCUMENTS 5,873,869 A * 2/1999 Hammons et al. .......... 604/369

FOREIGN PATENT DOCUMENTS

| EP | 0 512 010 B1 | 11/1992 | ........... A61F/13/15 |
| WO | WO 94/13704 | 6/1994 | ............. C97F/2/32 |

* cited by examiner

Primary Examiner—Dennis Ruhl
Assistant Examiner—C. Lynne Anderson
(74) Attorney, Agent, or Firm—Eileen L. Hughett; Jay A. Krebs; Ken K. Patel

(57) ABSTRACT

The present invention provides a liquid handling member that expands upon absorption of body liquid and contracts upon desorption of the body liquid. The liquid handling member of the present invention further exhibits an 80 percent absorption time of less than 2 seconds. The present invention further provides a device for handling body liquids which comprises the liquid handling member of the present invention.

15 Claims, 2 Drawing Sheets

DEVICE FOR MANAGING BODY FLUIDS COMPRISING A FAST ACQUIRING LIQUID HANDLING MEMBER THAT EXPANDS UPON LIQUID ACQUISITION AND CONTRACTS UPON LIQUID RELEASE

This is a continuation-in-part of application Ser. No. 09/646,076 filed Sep. 13, 2000.

FIELD OF THE INVENTION

The present invention relates to devices for managing body fluids such as urine, sweat, saliva, blood, menses, purulence, or fecal material, and in particular to their ability to acquire and retain aqueous based materials. The invention further relates to disposable absorbent articles such as baby diapers or training pants, adult incontinence products, and feminine hygiene products and other body liquid handling articles such as catheters, urinals, and the like.

BACKGROUND

Devices for managing body fluids are well known in the art and are frequently used for a wide variety of purposes. For example, the devices may serve hygienic purposes such as diapers, sanitary napkins, adult incontinence products, underarm sweat pads, and the like. There is another class of such devices which serve medical purposes such as wound dressings or drainages, catheters, and the like. Accordingly such devices have been designed to cope with a large variety of different body liquids such as for example urine, sweat, saliva, blood, menses, purulence, fecal material, and the like.

It has been recognized in the prior art that it is desirable to have large open pores in the acquisition region of the device to be able to readily accept body liquids into those voids even at high delivery rates. In addition, it has been recognized that, depending on the use, a large void volume for acquisition and intermediate storage of the liquid gushes is required close to the loading point. Large void volume, however, creates unwanted bulk for the device. The bulk thus created is particularly undesirable close to the body exits from which the body liquids are discharged such as the urethra. In order to limit the unwanted bulk at least before the first acquisition of body liquid, it has been suggested in the prior art to compress the acquisition material. Examples for this are acquisition patches comprising chemically stiffened cellulose which have been compressed in the moist condition in order to create hydrogen bonding to hold the material thin before discharge is acquired such as those disclosed for example in European patent publication No. 0 512 010 (Cook et al.). Upon the first wetting of such a material, however, these material tend to irreversibly expand. Hence, all such materials still create unwanted bulk for the remainder of the usage period. Other acquisition material its which are thin until wetted for the first time have been disclosed in PCT patent publication No. WO94/13704 which teaches a polymeric foam material commonly known as high internal phase emulsions. Some of the latter materials will re-contract upon dewatering, but those materials acquire liquid too slow to be useful for acquiring large gushes sufficiently fast.

It is an object of the present invention to provide a liquid handling member which overcomes the problems posed by the prior art.

It is a further object of the present invention to provide a liquid handling member which expands upon liquid absorption and contracts upon liquid desorption while having a short absorption time for the absorption of 80% of its total liquid capacity.

It is a further object of the present invention to provide a device for managing body liquids which comprises a liquid handling member of the present invention.

It is a further object of the present invention to provide disposable absorbent articles such as a baby diaper which comprises a liquid handling member according to the present invention.

SUMMARY OF THE INVENTION

The present invention provides a liquid handling member which is characterized in that said liquid handling member has a contraction factor of less than 0.8 after the first test cycle and an expansion factor of at least 1.25 after the first test cycle according to the reversible volume expansion test defined herein. The liquid handling member of the present invention further has a 80% absorption time of less than 2 seconds according to the Demand Absorbency Test defined herein.

It is another aspect of the present invention to provide a device for handling body liquids which comprises a liquid handling member according to the present invention.

DETAILED DESCRIPTION OF THE INVENTION

Figure 1A:
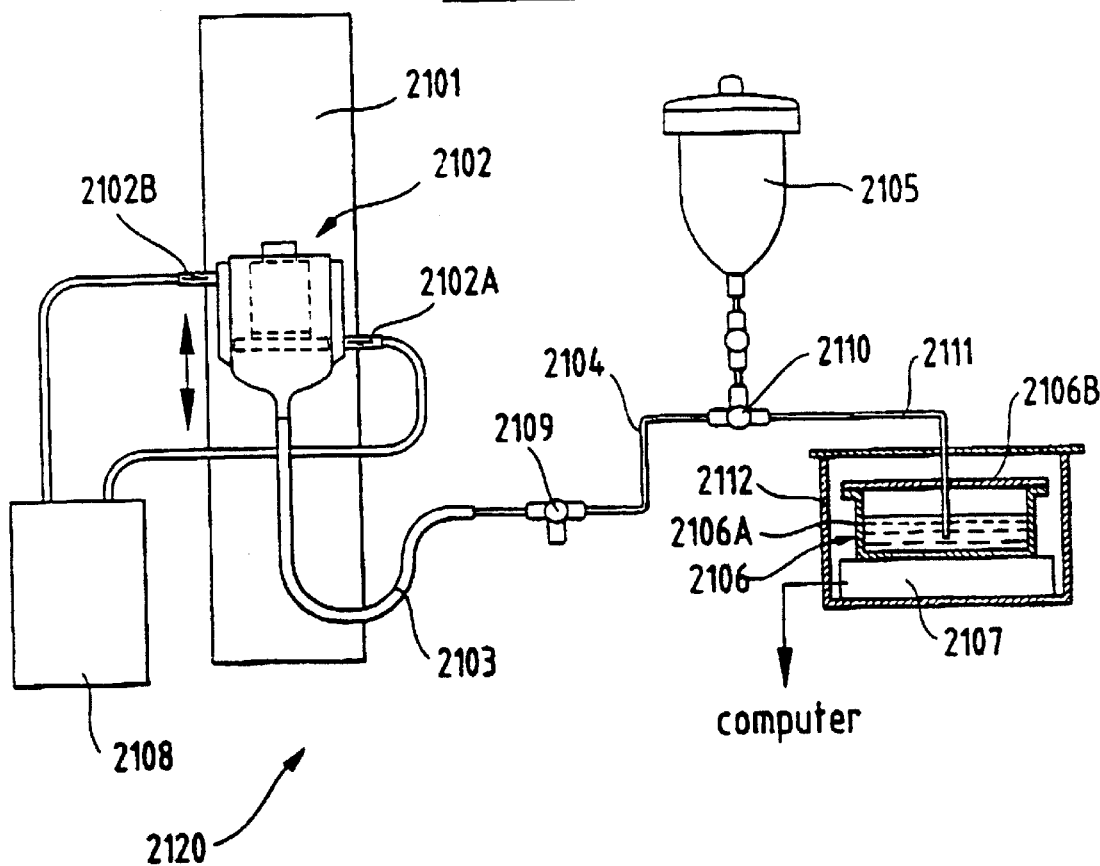
FIG. 1 shows a schematic drawing of the experimental setup for capillary sorption test.

The present invention is described in the following by means of a variety of different embodiments and by means of a variety of different features. Further embodiments of the present invention may be obtained by combining features of one embodiment with features of another embodiment disclosed herein and/or with other features disclosed herein. These further embodiments are considered to be implicitly disclosed herein and hence form part of-the present invention. It will be apparent to the skilled person that combinations of certain features may lead to non-functional articles not forming part of this present invention.

It is one aspect of the present invention to provide a liquid handling member which may be used for example in devices for handling body liquids such as diapers, training pants, sanitary napkins, adult incontinence devices and the like.

The term "liquid handling device" as used herein refers to devices which are designed to handle body liquids such as urine, blood, menses, sweat, saliva, feces, and the like. Handling body fluids includes but is not limited to acquiring, distributing, and storing the body liquids.

The liquid handling member of the present invention is designed to rapidly acquire body liquids. This capability may be quantified by the demand absorbency test defined hereinafter. The liquid handling member of the present invention has a 80 percent absorption time of less than 2 seconds, preferably a 80 percent absorption time of less than 1.5 second, more preferably a 80 percent absorption time of less than 1.25 seconds, most preferably a 80 percent absorption time of less than 1 second.

The liquid handling member of the present invention further exhibits an expansion contraction behavior that allows the liquid handling member to only have a high bulk when it is needed for body liquid acquisition and to have substantially reduced bulk when it is not needed. In particular, the liquid handling member of the present invention expands when liquid is absorbed such that the liquid handling member provides about as much bulk as is needed to acquire the body liquid. Furthermore, the liquid handling member of the present invention contracts again upon desorption of the previously acquired body liquid. In other words, the bulk of the liquid handling member of the present invention is reduced when the body liquid is removed again from the liquid handling member for example to be stored in a different region of the device for handling body liquids of the present invention. This expansion contraction behavior of the liquid handling member of the present invention is quantified by the reversible volume expansion test defined hereinafter. The liquid handling member of the present invention has a volume contraction factor of less than 0.8 after the first cycle, preferably of less than 0.7 after the first cycle, more preferably of less than 0.6 after the first cycle, most preferably of less than 0.5 after the first cycle. In addition the liquid handling member has a volume expansion factor of at least 1.25 after the first cycle, preferably of at least 1.43 after the first cycle, more preferably of at least 1.67 after the first cycle, and most preferably of at least 2.0 after the first cycle.

It is further desirable for the liquid handling member of the present invention to exhibit a similar expansion contraction behavior also for subsequent body liquid loadings. This capability can be quantified by running two absorption desorption cycles of the reversible volume expansion test defined hereinafter. Preferably, the liquid handling member of the present invention has a volume contraction factor of less than 0.9 of the second cycle more preferably of less than 0.8 after the first cycle, most preferably of less than 0.7 after the first cycle. Preferably, the liquid handling member of the present invention also has a volume expansion factor of at least 1.11 after the second cycle more preferably of at least 1.25 after the second cycle, and most preferably of at least 1.43 after the second cycle.

It is further desirable for the liquid handling member of the present invention in view of subsequent body liquid loadings, to not lose absorbent capacity on subsequent absorption desorption cycles. This capability can also be quantified by the reversible volume expansion test defined hereinafter. Preferably, the liquid handling member of the present invention has a capacity decrease factor of more than 0.7 after the first cycle more preferably of at least 0.8 after the first cycle, and most preferably of at least 0.9 after the first cycle. In addition, the liquid handling member of the present invention preferably has a capacity decrease factor of more than 0.5 after the second cycle, more preferably of at least 0.6 of the second cycle, and most preferably of at least 0.7 after the second cycle.

It is further desirable for the liquid handling member of the present invention to provide sufficient absorbent capacity to be able to completely acquire a gush of body liquid. Obviously, the size of a gush depends on the intended use of the liquid handling member or the respective device for handling body liquids. For example, the average gush size for toddlers in the weight range between nine and 18 kilograms is 75 milliliter, the 95 percentile of the gush size for this user group is at 110 milliliters. In contrast, the average gush size of adult incontinent persons is about 180 ml. For the purposes of this invention, the absorbent capacity of the liquid handling member of the present invention is be quantified by the demand absorbency test defined hereinafter. Preferably, the liquid handling member has an absorbent capacity of at least 80 percent of an average gush volume of the intended user group, more preferably an absorbent capacity of at least 100 percent of an average gush volume of the intended user group, most preferably an absorbent capacity equivalent to at least the 95 percentile of liquid gushes of intended user group.

In some embodiments of the present invention, the liquid handling member is intended to only temporarily store the acquired liquid. Accordingly, the liquid handling member must allow for liquid release sometime after the liquid acquisition into a liquid storage member. In this context, it is desirable for the liquid handling member of the present invention that only a low capillary pressure is needed for dewatering the liquid handling member. On the other hand, the liquid handling member must hold the acquired liquid in order to avoid immediate flow-back of the acquired liquid. Inventors have found a optimum desorption pressure range which is representative for this capability. The optimum medium desorption pressure is determined by the capillary sorption test defined hereinafter. Preferably, the liquid handling member of the present invention has a medium desorption pressure between 5 cm and 20 cm, more preferably between 5 cm and 15 cm, most preferably between 5 cm and 10 cm.

Optionally, the liquid handling member of the present invention has a high permeability in order to be able to efficiently transport the acquired liquid. For the purpose of this invention. For the purpose of this invention, this capability is quantified by the permeability test defined in PCT patent application Ser. No. US98/13497 filed on Jun. 29, 1998 incorporated herein by reference. Preferably, the liquid handling member of the present invention has a permeability of at least 10 Darcy, more preferably of at least 50 Darcy, most preferably of at least 100 Darcy.

In the following, a suitable embodiment of the liquid handling member will be described. The liquid handling member is assembled from an open celled foam material which is completely enveloped by a membrane. A suitable membrane material is available from SEFAR of Rüschlikon, Switzerland, under the designation SEFAR 03–20/14. A suitable foam material is available from Recticel of Brussels, Belgium, under the designation Bulpren S10 black. A suitable technique to completely envelope the foam material with the membrane material is to wrap the membrane material around the foam material and to subsequently heat seal all open edges of the membrane material. It will be readily apparent to the skilled practitioner to choose other similarly suitable materials. Depending on the specific intended application of the liquid handling member, it may also be required to choose similar materials with slightly different properties. After assembly, the liquid handling member is activated by immersing the liquid handling member in water or in synthetic urine until the liquid handling member is completely filled with liquid and until the membranes are completely wetted with liquid. After activation, a part of the liquid inside the liquid handling member may be squeezed out by applying an external pressure to the liquid handling member. If the activation of the liquid handling member was successful, the liquid handling member should not suck air through the membranes.

Other liquid handling members suitable for the purposes of the present invention are described for example in the PCT patent application Ser. No. PCT/US98/13497 entitled "Liquid transport member for high flux rates between two port regions" filed in the name of Ehrnsperger et al. filed on Jun. 29, 1998, and in the following PCT patent applications co-filed with the present application entitled "High flux liquid transport members comprising two different permeability regions" (P&G case CM1840MQ) filed in the name of Ehrnsperger et al., "Liquid transport member for high flux rates between two port regions" (P&G case CM1841 MQ) filed in the name of Ehrnsperger et al., "Liquid transport member for high flux rates against gravity" (P&G case CM1842MQ) filed in the name of Ehrnsperger et al., "Liquid transport member having high permeability bulk regions and high bubble point pressure port regions" (P&G case CM1843MQ) filed in the name of Ehrnsperger et al. All of these documents are enclosed herein by reference.

The particular geometry of the liquid handling member of the present invention can be varied according to the specific requirements of the intended application. If, for example, the liquid handling member is intended to be used in an absorbent article the liquid handling member may be defined such that its zone of intended liquid acquisition fits between the legs of the wearer and further that its intended liquid discharge zone matches the form of the storage member associated to it. Accordingly, the outer dimensions of the liquid handling member such as length, width, or thickness may also be adapted to the specific needs of the intended application. In this context, it has to be understood, however, that the design of the outer form of the liquid handling member may have an impact on its performance. For example, the cross section of the liquid handling member directly impacts on its permeability.

For application of the liquid handling member in a device for handling body liquids according to the present invention, the liquid handling member may be combined with a storage member. The term "liquid storage member" refers to a device which is capable of acquiring and storing liquid. The volume of the liquid storage member may vary with the amount of stored liquid such as by swelling. Typically, the storage member will imbibe the liquid by means of capillary suction and/or osmotic pressure. Other storage members may also use vacuum as a means to store the liquid. The liquid storage member is further capable of holding at least a portion of the stored liquid under pressure. Suitable storage members are well known in the art and may comprise for example a super absorbent polymeric material such as polyacrylate. The storage member may further comprise a fibrous structure, such as a pad of cellulosic fibers, in which the particulate superabsorbent material is dispersed. A suitable storage member is for example a superabsorbent polymer such as available from CHEMDAL, United Kingdom, under the designation ASAP400. Further examples of suitable superabsorbent polymers, often also referred to as "hydrogel forming polymer" or "absorbent gelling material", are described in U.S. Pat. No. 5,562,646 (Goldman et al.), issued Oct. 8, 1996 and U.S. Pat. No. 5,599,335 (Goldman et al.), issued Feb. 4, 1997.

In order to pick up the liquid discharged from the liquid handling member, the storage member may be placed in direct liquid communication with the intended liquid discharge zone of the liquid handling member.

In one embodiment of the present invention, the liquid handling member of the present invention is geometrically saturated or substantially geometrically saturated with free liquid. The term "free liquid" as used herein refers to liquid which is not bound to a specific surface or other entity. Free liquid can be distinguished from bound liquid by measuring the proton spin relaxation time $T_2$ of the liquid molecules a according to NMR (nuclear magnetic resonance) spectroscopy methods well known in the art.

The term "geometrically saturated" as used herein refers to a region of a porous material in which the liquid accessible void spaces have been filled with a liquid. The void spaces referred to in this definition are those which are present in the current geometric configuration of the porous material. In other words, a geometrically saturated device may still be able to accept additional liquid by and only by changing its geometric configuration for example by swelling, although all voids of the device are filled with liquid in the current geometric configuration. A device for handling liquids is called geometrically saturated, if all porous materials that are part of the device and intended for liquid handling are geometrically saturated.

The term "porous material" as used herein refers to materials that comprise at least two phases a solid material and a gas or void phase—and optionally a third liquid phase that may be partially or completely filling said void spaces. The porosity of a material is defined as the ratio between the void volume and the total volume of the material, measured when the material is not filled with liquid. Non-limiting examples for porous materials are foams such as polyurethane, HIPE (see for example PCT patent application WO94/13704), superabsorbent foams and the like, fiber assemblies such as meltblown, spunbond, carded, cellulose webs, fiber beds and the like, porous particles such as clay, zeolites, and the like, geometrically structured materials such as tubes, balloons, channel structures etc. Porous materials might absorb liquids even if they are not hydrophilic. The porosity of the materials is therefore not linked to their affinity for the liquid that might be absorbed.

The term "substantially geometrically saturated" as used herein refers to a member in which at least 90% of the macroscopic void volume of the member are geometrically saturated, preferably at least 95% of the macroscopic void volume of the device are geometrically saturated, more preferably 97% of the macroscopic void volume of the device are geometrically saturated, most preferably 99% of the macroscopic void volume of the device are geometrically saturated.

Device for Handling Body Liquid

It is one aspect of the present invention to provide a device for handling body liquids which comprises a liquid transport member according to the present invention. Such devices include but are not limited to disposable absorbent articles such as baby diapers or training pants, adult incontinence products, and feminine hygiene products and other body liquid handling articles such as catheters, urinals, and the like.

In one embodiment of the present invention, the device for handling body liquids is a disposable absorbent article such as a diaper, a training pant, a sanitary napkin, an adult incontinence device, or the like. Such an absorbent article may further comprise a liquid pervious topsheet, a liquid impervious backsheet at least partially peripherally joined to the topsheet. The absorbent article may further comprise an absorbent core which may serve as a storage member for the body liquid. Topsheets, backsheet, and absorbent cores suitable for the present invention are well known in the art. In addition, there are numerous additional features known in the art which can be used in combination with the absorbent article of the present invention such as for example closure mechanisms to attach the absorbent article around the lower torso of the wearer.

METHODS

Unless stated otherwise, all tests are carried out at about 32° C.+/−2° C. and at 35+/−15% relative humidity.

Unless stated otherwise, the synthetic urine used in the test methods is commonly known as Jayco SynUrine and is available from Jayco Pharmaceuticals Company of Camp Hill, Pa. The formula for the synthetic urine is: 2.0 g/: of KCl; 2.0 g/l of Na2SO4; 0.85 g/l of (NH4)H2PO4; 0.15 g/l (NH4)H2PO4; 0.19 g/l of CaCl2; ad 0.23 g/l of MgCl2. All of the chemicals are of reagent grade. The pH of the synthetic Urine is in the range of 6.0 to 6.4.

Demand Absorbency Test

The demand absorbency test is intended to measure the liquid capacity of liquid handling member and to measure the absorption speed of liquid handling member against zero hydrostatic pressure. The test may also be carried out for devices for managing body liquids containing a liquid handling member.

The apparatus used to conduct this test consists of a square basket of a sufficient size to hold the liquid handling member suspended on a frame. At least the lower plane of the square basket consists of an open mesh that allows liquid penetration into the basket without substantial flow resistance for the liquid uptake. For example, an open wire mesh made of stainless steel having an open area of at least 70 percent and having a wire diameter of 1 mm, and an open mesh size of at about 6 mm is suitable for the setup of the present test. In addition, the open mesh should exhibit sufficient stability such that it substantially does not deform under load of the test specimen when the test specimen is filled up to its full capacity.

Below the basket, a liquid reservoir is provided. The height of the basket can be adjusted so that a test specimen which is placed inside the basket may be brought into contact with the surface of the liquid in the liquid reservoir. The liquid reservoir is placed on the electronic balance connected to a computer to read out the weight of the liquid about every 0.01 sec during the measurement. The dimensions of the apparatus are chosen such that the liquid handling member to be tested fits into the basket and such that the intended liquid acquisition zone of the liquid handling member is in contact with the lower plane of the basket. The dimensions of the liquid reservoir are chosen such that the level of the liquid surface in the reservoir does not substantially change during the measurement. A typical reservoir useful for testing liquid handling members has a size of at least 320 mm×370 mm and can hold at least about 4500 g of liquid.

Before the test, the liquid reservoir is filled with synthetic urine. The amount of synthetic urine and the size of the liquid reservoir should be sufficient such that the liquid level in the reservoir does not change when the liquid capacity of the liquid handling member to be tested is removed from the reservoir.

The temperature of the liquid and the environment for the test should reflect in-use conditions of the member. Typical temperature for use in baby diapers are 32 degrees Celsius for the environment and 37 degrees Celsius for the synthetic urine. The test may be done at room temperature if the member tested has no significant dependence of its absorbent properties on temperature.

The test is setup by lowering the empty basket until the mesh is just completely immersed in the synthetic urine in the reservoir. The basket is then raised again by about 0.5 to 1 mm in order to establish an almost zero hydrostatic suction, care should be taken that the liquid stays in contact with the mesh. If necessary, the mesh needs to be brought back into contact with the liquid and zero level be readjusted.

The Test is Started By:
1. starting the measurement of the electronic balance;
2. placing the liquid handling member on the mesh such that the acquisition zone of the member is in contact with the liquid;
3. immediately adding a low weigh on top of the member in order to provide a pressure of 165 Pa for better contact of the member to the mesh.

During the test, the liquid uptake by the liquid handing member is recorded by measuring the weight decrease of the liquid in the liquid reservoir. The test is stopped after 30 minutes.

At the end of the test, the total liquid uptake of the liquid handing member is recorded. In addition, the time after which the liquid handling member had absorbed 80 percent of its total liquid uptake is recorded. The zero time is defined as the time where the absorption of the member starts. The initial absorption speed of the liquid handling member is from the initial linear slope of the weight vs. time measurement curve.

Capillary Sorption Test

Purpose

The purpose of this test is to measure the capillary sorption absorbent capacity, as a function of height, of liquid handling members of the present invention. This test may also be used to measure the capillary sorption absorbent capacity of devices for handling body liquids according to the present invention. Capillary sorption is a fundamental property of any absorbent that governs how liquid is absorbed into the absorbent structure. In the Capillary Sorption experiment, capillary sorption absorbent capacity is measured as a function of fluid pressure due to the height of the sample relative to the test fluid reservoir.

The method for determining capillary sorption is well recognized. See Burgeni, A. A. and Kapur, C., "Capillary Sorption Equilibria in Fiber Masses," Textile Research Journal, 37 (1967), 356–366; Chatterjee, P. K., Absorbency, Textile Science and Technology 7, Chapter II, pp 29–84, Elsevier Science Publishers B. V, 1985; and U.S. Pat. No. 4,610,678, issued Sep. 9, 1986 to Weisman et al. for a discussion of the method for measuring capillary sorption of absorbent structures. The disclosure of each of these references is incorporated by reference herein.

Principle

A porous glass frit is connected via an uninterrupted column of fluid to a fluid reservoir on a balance. The sample is maintained under a constant confining weight during the experiment. As the porous structure absorbs fluid upon demand, the weight loss in the balance fluid reservoir is recorded as fluid uptake, adjusted for uptake of the glass frit as a function of height and evaporation. The uptake or capacity at various capillary suctions (hydrostatic tensions or heights) is measured. Incremental absorption occurs due to the incremental lowering of the frit (i.e., decreasing capillary suction).

Time is also monitored during the experiment to enable calculation of initial effective uptake rate (g/g/h) at a 200 cm height.

Reagents

Test Liquid: Synthetic urine is prepared by completely dissolving the following materials in distilled water.

| Compound | F.W. | Concentration (g/L) |
| --- | --- | --- |
| KCl | 74.6 | 2.0 |
| $Na_2SO_4$ | 142 | 2.0 |
| $(NH_4)H_2PO_4$ | 115 | 0.85 |
| $(NH_4)_2HPO_4$ | 132 | 0.15 |
| $CaCl_2.2H_2O$ | 147 | 0.25 |
| $MgCl_2.6H_2O$ | 203 | 0.5 |

General Description of Apparatus Set Up

Figure 1D:
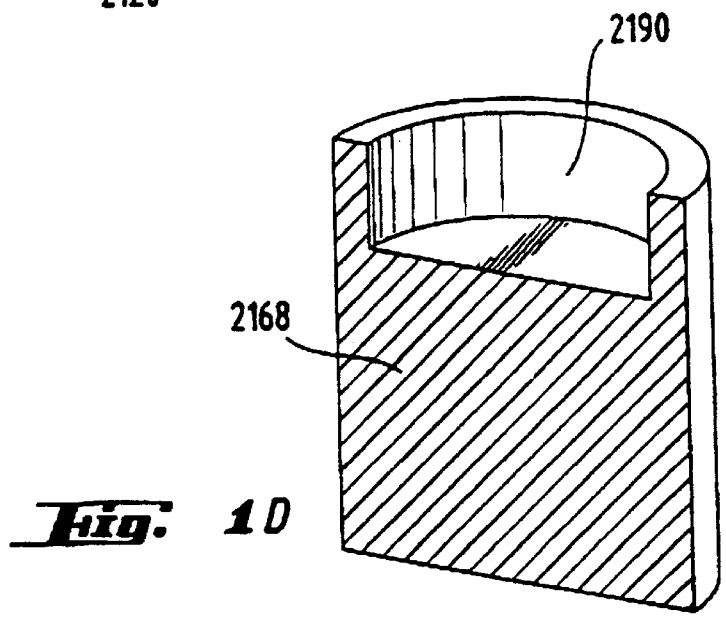
Figure 1B:
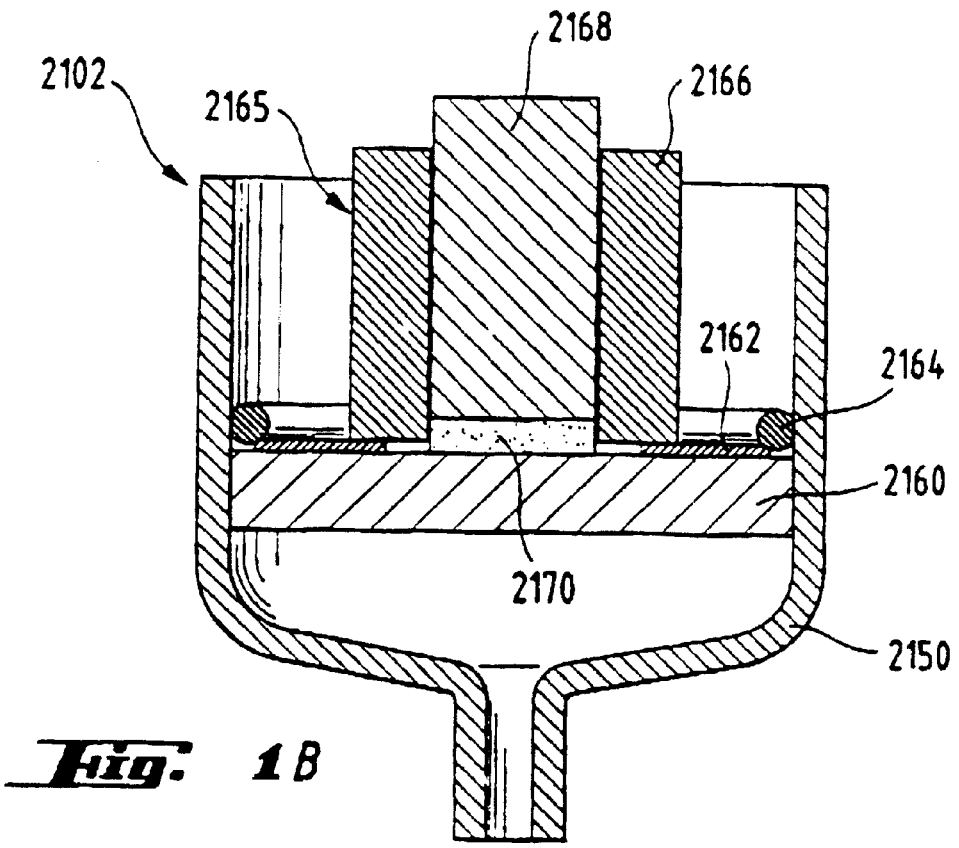
Figure 1C:
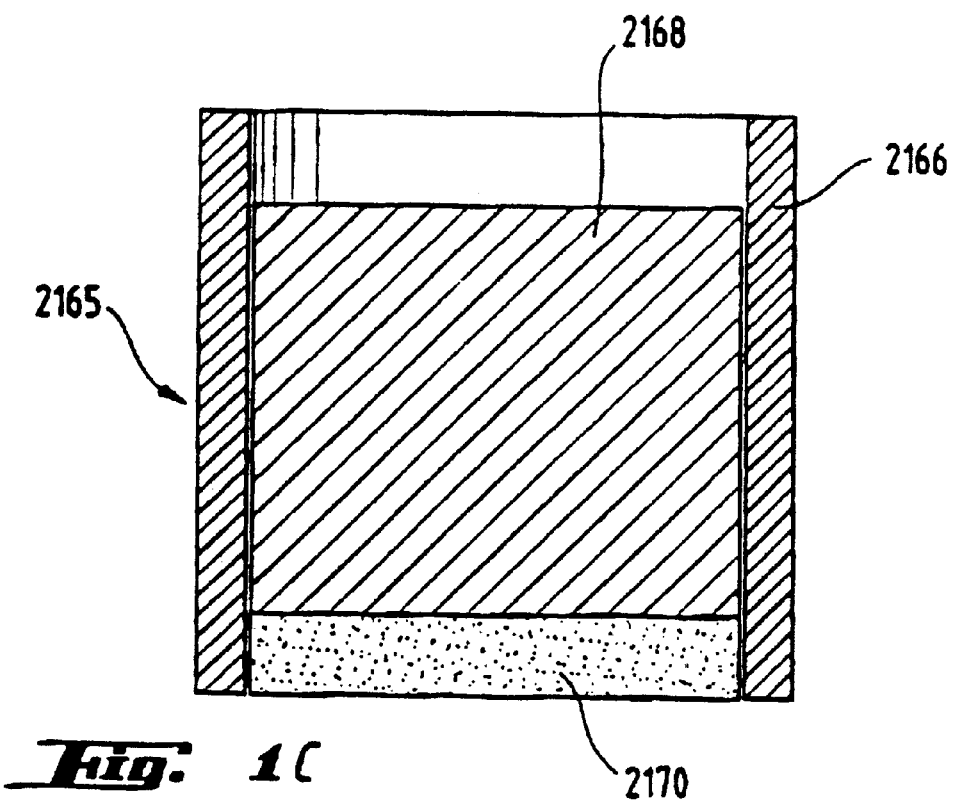

The Capillary Sorption equipment, depicted generally as 520 in FIG. 1, used for this test is operated under TAPPI conditions (50% RH, 25° C.). A test sample is placed on a glass frit shown in FIG. 1 as 502 that is connected via a continuous column of test liquid (synthetic urine) to a balance liquid reservoir, shown as 506, containing test liquid. This reservoir 506 is placed on a balance 507 that is interfaced with a computer (not shown). The balance should be capable of reading to 0.001 g; such a balance is available from Mettler Toledo as PR1203 (Hightstown, N.J.). The glass frit 502 is placed on a vertical slide, shown generally in FIG. 1 as 501, to allow vertical movement of the test sample to expose the test sample to varying suction heights. The vertical slide may be a rodless actuator which is attached to a computer to record suction heights and corresponding times for measuring liquid uptake by the test sample. A preferred rodless actuator is available from industrial Devices (Novato, Calif.) as item 202X4X34N-1D4B-84-P-C-S-E, which may be powered by motor drive ZETA 6104-83-135, available from CompuMotor (Rohnert, Calif.). Where data is measured and sent from actuator 501 and balance 507, capillary sorption absorbent capacity data may be readily generated for each test sample. Also, computer interface to actuator 501 may allow for controlled vertical movement of the glass frit 502. For example, the actuator may be directed to move the glass frit 502 vertically only after "equilibrium" (as defined below) is reached at each suction height.

The bottom of glass frit 502 is connected to Tygon® tubing 503 that connects the frit 505 to three-way drain stopcock 509. Drain stopcock 509 is connected to liquid reservoir 505 via glass tubing 504 and stopcock 510. (The stopcock 509 is open to the drain only during cleaning of the apparatus or air bubble removal.) Glass tubing 511 connects fluid reservoir 505 with balance fluid reservoir 506, via stopcock 510. Balance liquid reservoir 506 may consist of a lightweight 12 cm diameter glass dish 506A and cover 506B. The cover 506B has a hole through which glass tubing 511 contacts the liquid in the reservoir 506. The glass tubing 511 must not contact the cover 506B or an unstable balance reading will result and the test sample measurement cannot be used. In this context, it is to be understood that the volume of the liquid reservoir needs to be compatible with the absorbent capacity of the liquid handing member or the device to be tested. Hence, it may be necessary to choose a different liquid reservoir.

The glass frit diameter must be sufficient to accommodate the piston/cylinder apparatus, discussed below, for holding the test sample. The glass frit 502 is jacketed to allow for a constant temperature control from a heating bath. A suitable frit is a 350 ml fritted disc funnel specified as having 4 to 5.5 mm pores, available from Corning Glass Co. (Coming, N.Y.) as #36060-350F. The pores are fine enough to keep the frit surface wetted at capillary suction heights specified (the glass frit does not allow air to enter the continuous column of test liquid below the glass frit).

As indicated, the frit 502 is connected via tubing to fluid reservoir 505 or balance liquid reservoir 506, depending on the position of three-way stopcock 510.

Glass frit 502 is jacketed to accept water from a constant temperature bath. This will ensure that the temperature of the glass frit is kept at a constant temperature of 88° F. (31° C.) during the testing procedure. As is depicted in FIG. 1, the glass frit 502 is equipped with an inlet port 502A and outlet port 502B, which make a closed loop with a circulating heat bath shown generally as 508. (The glass jacketing is not depicted in FIG. 1. However, the water introduced to the jacketed glass frit 502 from bath 508 does not contact the test liquid and the test liquid is not circulated through the constant temperature bath. The water in the constant temperature bath circulates through the jacketed walls of the glass frit 502.)

Reservoir 506 and balance 507 are enclosed in a box to minimize evaporation of test liquid from the balance reservoir and to enhance balance stability during performance of the experiment. This box, shown generally as 512, has a top and walls, where the top has a hole through which tubing 511 is inserted.

The glass frit 502 is shown in more detail in FIG. 2B. FIG. 2B is a cross-sectional view of the glass frit, shown without inlet port 502A and outlet port 502B. As indicated, the glass frit is a 350 ml fritted disc funnel having specified 4 to 5.5 mm pores. Referring to FIG. 2B, the glass frit 502 comprises a cylindrical jacketed funnel designated as 550 and a glass frit disc shown as 560. The glass frit 502 further comprises a cylinder/piston assembly shown generally as 565 (which comprises cylinder 566 and piston 568), which confines the test sample, shown as 570, and provides a small confining pressure to the test sample. To prevent excessive evaporation of test liquid from the glass frit disc 560, a Teflon ring shown as 562 is placed on top of the glass frit disc 560. The Teflone O ring 562 is 0.0127 cm thick (available as sheet stock from McMasterCarr as #8569K16 and is cut to size) and is used to cover the frit disc surface outside of the cylinder 566, and thus minimizes evaporation from the glass frit. The ring outer diameter and inner diameter is 7.6 and 6.3 cm, respectively. The inner diameter of the Teflon® ring 562 is about 2 mm less than the outer diameter of cylinder 566. A Viton® O-ring (available from McMasterCarr as #AS568A-150 and AS568A-151) 564 is placed on top of Teflon® ring 562 to seal the space between the inner wall of cylindrical jacketed funnel 550 and Teflon® ring 562, to further assist in prevention of evaporation. If the O-ring outer diameter exceeds the inner diameter of cylindrical jacketed funnel 550, the O-ring diameter is reduced to fit the funnel as follows: the O-ring is cut open, the necessary amount of O-ring material is cut off, and the O-ring is glued back together such that the O-ring contacts the inner wall of the cylindrical jacketed funnel 550 all around its periphery. While the above described frit represents one suitable example of frit, it may be necessary to use of frit having dimensions different from the above dimensions in order to better fit the dimensions of the liquid handling member or the device to be tested. The surface area of the frit should resemble as closely as possible the surface area of the acquisition zone of the liquid handling member or the device in order to fully use the acquisition zone and in order to minimize the evaporation from the frit.

As indicated, a cylinder/piston assembly shown generally in FIG. 2B as 565 confines the test sample and provides a small confining pressure to the test sample 570. Referring to FIG. 2C, assembly 565 consists of a cylinder 566, a cup-like Teflon® piston indicated by 568 and, when necessary, a weight or weights (not shown) that fits inside piston 568. (Optional weight will be used when necessary to adjust the combined weight of the piston and the optional weight so a confining pressure of 0.2 psi is attained depending on the test sample's dry diameter. This is discussed below.) The cylinder 566 is Lexan® bar stock and has the following dimensions: an outer diameter of 7.0 cm, an inner diameter of 6.0 cm and a height of 6.0 cm. The Teflon® piston 568 has the following dimensions: an outer diameter that is 0.02 cm less than the inner diameter of cylinder 566. As shown in FIG. 2D, the end of the piston 568 that does not contact the test sample is bored to provide a 5.0 cm diameter by about 1.8 cm deep chamber 590 to receive optional weights (dictated by the test sample's actual dry diameter) required to attain a test sample confining pressure of 0.2 psi (1.4 kPa). In other words, the total weight of the piston 568 and any optional weights (not shown in FIGS.) divided by the test sample's actual diameter (when dry) should be such that a confining pressure of 0.2 psi is attained. Cylinder 566 and piston 568 (and optional weights) are equilibrated at 31° C. for at least 30 minutes prior to conducting the capillary sorption absorbent capacity measurement. Again, the above described dimensions are chosen to fit the above described exemplary frit. Of course, when a different frit is chosen the dimensions of the cylinder/piston assembly need to be adjusted accordingly.

A non-surfactant treated or incorporated apertured film (14 cm×14 cm) (not shown) is used to cover the glass frit 502 during Capillary Sorption experiments to minimize air destablization around the sample. Apertures are large enough to prevent condensation from forming on the underside of the film during the experiment.

Test Sample Preparation

For the present procedure, it is important, that the dimensions of the sample and of the frit should not be too different. To achieve this, two approaches can be taken:

a) For test samples, which can be readily adjusted to a suitable size, such as by cutting these, both the size of this cutting as well as of the frit are chosen to be a circular shaped structure of 5.4 cm diameter, such as can be done by using a conventional arc punch.

b) When the test sample cannot readily be cut to this dimension, the size and preferably also the shape of the frit has to be adjusted to the size and shape of the test sample.

In both cases, the test sample can be a readily separatable element of a member or a device, it can be a particular component of any of these, or can be a combination of components thereof. It might also be necessary to adjust the size of the liquid reservoir to match the varying requirements.

The dry weight of the test sample (used below to calculate capillary sorption absorbent capacity) is the weight of the test sample prepared as above under ambient conditions.

Experimental Set Up

1. Place a clean, dry glass frit 502 in a funnel holder attached to the vertical slide 501. Move the funnel holder of the vertical slide such that the glass frit is at the 0 cm height.
2. Set up the apparatus components as shown in FIG. 1, as discussed above.
3. Place 12 cm diameter balance liquid reservoir 506 on the balance 507. Place plastic lid 506B over this balance liquid reservoir 506 and a plastic lid over the balance box 512 each with small holes to allow the glass tubing 511 to fit through. Do not allow the glass tubing to touch the lid 506B of the balance liquid reservoir or an unstable balance reading will result and the measurement cannot be used.
4. Stopcock 510 is closed to tubing 504 and opened to glass tubing 511. Fluid reservoir 505, previously filled with test fluid, is opened to allow test fluid to enter tubing 511, to fill balance fluid reservoir 506.
5. The glass frit 502 is leveled and secured in place. Also, ensure that the glass frit is dry.
6. Attach the TygonÒ tubing 503 to stopcock 509. (The tubing should be long enough to reach the glass frit 502 at its highest point of 200 cm with no kinks.) Fill this TygonÒ tubing with test liquid from liquid reservoir 505.
7. Attach the TygonÒ tubing 503 to the level glass frit 502 and then open stopcock 509 and stopcock 510 leading from fluid reservoir 505 to the glass frit 502. (Stopcock 510 should be closed to glass tubing 511.) The test liquid fills the glass frit 502 and removes all trapped air during filling of the level glass frit. Continue to fill until the fluid level exceeds the top of the glass frit disc 560. Empty the funnel and remove all air bubbles in the tubing and inside the funnel. Air bubbles may be removed by inverting glass frit 502 and allowing air bubbles to rise and escape through the drain of stopcock 509. (Air bubbles typically collect on the bottom of the glass frit disc 560.) Relevel the frit using a small enough level that it will fit inside the jacketed funnel 550 and onto the surface of glass frit disc 560.
8. Zero the glass frit with the balance liquid reservoir 506.

To do this, take a piece of TygonÒ tubing of sufficient length and fill it with the test liquid. Place one end in the balance liquid reservoir 506 and use the other end to position the glass frit 502. The test liquid level indicated by the tubing (which is equivalent to the balance liquid reservoir level) is 10 mm below the top of the glass frit disc 560. If this is not the case, either adjust the amount of liquid in the reservoir or reset the zero position on the vertical slide 501.
9. Attach the outlet and inlet ports from the temperature bath 508 via tubing to the inlet and outlet ports 502A and 502B, respectively, of the glass frit. Allow the temperature of the glass frit disc 560 to come to 31° C. This can be measured by partially filling the glass frit with test liquid and measuring its temperature after it has reached equilibrium temperature. The bath will need to be set a bit higher than 31° C. to allow for the dissipation of heat during the travel of water from the bath to the glass frit.
10. The glass frit is equilibrated for 30 minutes.

Capillary Sorption Parameters

The following describes a computer program that will determine how long the glass frit remains at each height.

In the capillary sorption software program, a test sample is at some specified height from the reservoir of fluid. As indicated above, the fluid reservoir is on a balance, such that a computer can read the balance at the end of a known time interval and calculate the flow rate (Delta reading/time interval) between the test sample and reservoir. For purposes of this method, the test sample is considered to be at equilibrium when the flow rate is less than a specified flow rate for a specified number of consecutive time intervals. It is recognized, that for certain material, actual equilibrium may not be reached when the specified "EQUILIBRIUM CONSTANT" is reached. The time interval between readings is 5 seconds.

The number of readings in the delta table is specified in the capillary sorption menu as "EQUILIBRIUM SAMPLES". The maximum number of deltas is 500. The flow rate constant is specified in the capillary sorption menu as "EQUILIBRIUM CONSTANT".

The Equilibrium Constant is entered in units of grams/sec, ranging from 0.0001 to 100.000.

The following is a simplified example of the logic. The table shows the balance reading and Delta Flow calculated for each Time Interval.

Equilibrium Samples=3

| Time Interval | Equilibrium Constant = 0.0015 | |
|---|---|---|
| | Balance Value (g) | Delta Flow (g/sec) |
| 0 | 0 | |
| 1 | 0.090 | 0.0180 |
| 2 | 0.165 | 0.0150 |
| 3 | 0.225 | 0.0120 |
| 4 | 0.270 | 0.0090 |
| 5 | 0.295 | 0.0050 |
| 6 | 0.305 | 0.0020 |
| 7 | 0.312 | 0.0014 |
| 8 | 0.316 | 0.0008 |
| 9 | 0.318 | 0.0004 |

Delta Table:

| | Time | | | | | | | | | |
|---|---|---|---|---|---|---|---|---|---|---|
| | 0 | 1 | 2 | 3 | 4 | 5 | 6 | 7 | 8 | 9 |
| Delta 1 | 9999 | 0.0180 | 0.0180 | 0.0180 | 0.0090 | 0.0090 | 0.0090 | 0.0014 | 0.0014 | 0.0014 |
| Delta 2 | 9999 | 9999 | 0.0150 | 0.0150 | 0.0150 | 0.0050 | 0.0050 | 0.0050 | 0.0008 | 0.0008 |
| Delta 3 | 9999 | 9999 | 9999 | 0.0120 | 0.0120 | 0.0120 | 0.0020 | 0.0020 | 0.0020 | 0.0004 |

The equilibrium uptake for the above simplified example is 0.318 gram.

The following is the code in C language used to determine equilibrium uptake:

```
/*                 takedata.c                     */
int take_data(int equil_samples,double equilibrium_constant)
{
double   delta;
static   double deltas[500];      /* table to store up to 500 deltas */
double   value;
double   prev_value;
clock_t next_time;
int   i;
for (i=0; i<equil_samples; i++)
     deltas[i] = 9999.;           /* initialize all values in the delta table to 9999. gms/sec */
delta_table_index = 0;            /* initialize where in the table to store the next delta */
equilibrium_reached = 0;          /* initialize flag to indicate equilibrium has not been
reached */
next_= clock();                   /* initialize when to take the next reading */
prev_reading = 0;                 /* initialize the value of the previous reading from the balance
*/
while (!equilibrium_reached) {    /* start of loop for checking for equilibrium */
     next_time += 5000L;          /* calculate when to take next reading */
     while (clock() < next_time); /* wait until 5 seconds has elapsed from prev reading */
     value = get_balance_reading();  /* read the balance in grams */
     delta = fabs(prev_value - value)/5.0;  /* calculate absolute value of flow in last 5 seconds */
     prev_value = value;          /* store current value for next loop */
     deltas[delta_table_index] = delta;    /* store current delta value in the table of deltas */
     delta_table_index++;         /* increment pointer to next position in table */
         if (delta_table_index == equil_samples)   /* when the number of deltas = the number of */
            delta_table_index = 0;  /* equilibrium samples specified, /*
                                  /* reset the pointer to the start of the table. This way */
                                  /* the table always contains the last xx current samples. */
     equilibrium_reached = 1;     /* set the flag to indicate equilibrium is reached */
     for (i=0; i < equil_samples; i++)    /* check all the values in the delta table */
         if (deltas[i] >= equilibrium_constant)  /* if any value is > or = to the equilibrium constant */
            equilibrium_reached = 0;  /* set the equilibrium flag to 0 (not at equilibrium) */
     }                            /* go back to the start of the loop */
}
```

Capillary Sorption Parameters
  Load Description (Confining Pressure): 0.2 psi load
  Equilibrium Samples (n): 50
  Equilibrium Constant: 0.0005 g/sec
  Setup Height Value: 100 cm
  Finish Height Value: 0 cm
  Hydrostatic Head Parameters: 200, 180, 160, 140, 120, 100, 90, 80, 70, 60, 50, 45, 40, 35, 30, 25, 20, 15, 10, 5 and 0 cm.

The capillary sorption procedure is conducted using all the heights specified above, in the order stated, for the measurement of capillary sorption absorbent capacity. Even if it is desired to determine capillary sorption absorbent capacity at a particular height (e.g., 35 cm), the entire series of hydrostatic head parameters must be completed in the order specified. Although all these heights are used in performance of the capillary sorption test to generate capillary sorption isotherms for a test sample, the present disclosure describes the storage absorbent members in terms of their absorbent properties at specified heights of 200, 140, 100, 50, 35 and 0 cm.

Capillary Sorption Procedure
  1) Follow the experimental setup procedure.
  2) Make sure the temperature bath 508 is on and water is circulating through the glass frit 502 and that the glass frit disc 560 temperature is 31+ C.
  3) Position glass frit 502 at 200 cm suction height. Open stopcocks 509 and 510 to connect glass frit 502 with the balance liquid reservoir 506. (Stopcock 510 is closed to liquid reservoir 505.) Glass frit 502 is equilibrated for 30 minutes.
  4) Input the above capillary sorption parameters into the computer.
  5) Close stopcocks 509 and 510.
  6) Move glass frit 502 to the set up height, 100 cm.
  7) Place Teflon® ring 562 on surface of glass frit disc 560. Put O-ring 564 on Teflon® ring. Place pre-heated cylinder 566 concentrically on the Teflon® ring. Place test sample 570 concentrically in cylinder 566 on glass frit disc 560. Place piston 568 into cylinder 566. Additional confining weights are placed into piston chamber 590, if required.
  8) Cover the glass frit 502 with apertured film.
  9) The balance reading at this point establishes the zero or tare reading.
  10) Move the glass frit 502 to 200 cm.
  11) Open stopcocks 509 and 510 (stopcock 510 is closed to fluid reservoir 505) and begin balance and time readings.

Glass Frit Correction (Blank Correct Uptake)

Since the glass frit disc 560 is a porous structure, the glass frit (502) capillary sorption absorption uptake (blank correct uptake) must be determined and subtracted to get the true test sample capillary sorption absorption uptake. The glass frit correction is performed for each new glass frit used. Run the capillary sorption procedure as described above, except without test sample, to obtain the Blank Uptake (g). The elapsed time at each specified height equals the Blank Time (s).

Evaporation Loss Correction
  1) Move the glass frit 502 to 2 cm above zero and let it equilibrate at this height for 30 minutes with open stopcocks 509 and 510 (closed to reservoir 505).
  2) Close stopcocks 509 and 510.
  3) Place Teflon® ring 562 on surface of glass frit disc 560. Put O-ring 564 on Teflon® ring. Place pre-heated cylinder 566 concentrically on the Teflon® ring. Place piston 568 into cylinder 566. Place apertured film on glass frit 502.
  4) Open stopcocks 509 and 510 (closed to reservoir 505) and record balance reading and time for 3.5 hours. Calculate Sample Evaporation (g/hr) as follows:
  [Balance Reading at 1 hr–balance reading at 3.5 hr]/2.5 hr Even after taking all the above precautions, some evaporative loss will occur, typically around 0.10 gm/hr for both the test sample and the frit correction. Ideally, the sample evaporation is measured for each newly installed glass frit 502.

Cleaning the Equipment

New Tygon⊙ tubing 503 is used when a glass frit 502 is newly installed. Glass tubing 504 and 511, fluid reservoir 505, and balance liquid reservoir 506 are cleaned with 50% Clorox Bleach® in distilled water, followed by distilled water rinse, if microbial contamination is visible.

a. Cleaning After Each Experiment

At the end of each experiment (after the test sample has been removed), the glass frit is forward flushed (i.e., test liquid is introduced into the bottom of the glass frit) with 250 ml test liquid from liquid reservoir 505 to remove residual test sample from the glass frit disc pores. With stopcocks 509 and 510 open to liquid reservoir 505 and closed to balance liquid reservoir 506, the glass frit is removed from its holder, turned upside down and is rinsed out first with test liquid, followed by rinses with acetone and test liquid (synthetic urine). During rinsing, the glass frit must be tilted upside down and rinse fluid is squirted onto the test sample contacting surface of the glass frit disc. After rinsing, the glass frit is forward flushed a second time with 250 ml test liquid (synthetic urine). Finally, the glass frit is reinstalled in its holder and the frit surface is leveled.

b. Monitoring Glass Frit Performance

Glass frit performance must be monitored after each cleaning procedure and for each newly installed glass frit, with the glass frit set up at 0 cm position. 50 ml of test liquid are poured onto the leveled glass frit disc surface (without Teflon® ring, O-ring and the cylinder/piston components). The time it takes for the test fluid level to drop to 5 mm above the glass frit disc surface is recorded. A periodic cleaning must be performed if this time exceeds 4.5 minutes.

c. Periodic Cleaning

Periodically, (see monitoring frit performance, above) the glass frits are cleaned thoroughly to prevent clogging. Rinsing fluids are distilled water, acetone, 50% Clorox Bleach® in distilled water (to remove bacterial growth) and test liquid. Cleaning involves removing the glass frit from the holder and disconnecting all tubing. The glass frit is forward flushed (i.e., rinse liquid is introduced into the bottom of the glass frit) with the frit upside down with the appropriate fluids and amounts in the following order:
  1. 250 ml distilled water.
  2. 100 ml acetone.
  3. 250 ml distilled water.
  4. 100 ml 50:50 Clorox®/distilled water solution.
  5. 250 ml distilled water.
  6. 250 ml test fluid.

The cleaning procedure is satisfactory when glass frit performance is within the set criteria of fluid flow (see above) and when no residue is observable on the glass frit disc surface. If cleaning can not be performed successfully, the frit must be replaced.

Calculations

The computer is set up to provide a report consisting of the capillary suction height in cm, time, and the uptake in grams at each specified height. From this data, the capillary suction absorbent capacity, which is corrected for both the frit uptake and the evaporation loss, can be calculated. Also, based on the capillary suction absorbent capacity at 0 cm, the capillary absorption efficiency can be calculated at the specified heights. In addition, the initial effective uptake rate at 200 cm is calculated.

Blank Correct Uptake $$\text{Blank Correct Uptake (g)} = \text{Blank Uptake (g)} - \frac{\text{Blank Time (s)} \ast \text{Blank Evap. (g/hr)}}{3600 \text{ (s/hr)}}$$

Capillary Suction Absorbent Capacity ("CSAC")

$$\text{Net Uptake (g/g)} = \frac{\text{Sample Uptake (g)} - \frac{\text{Sample Time (s)} \ast \text{Sample Evap. (g/hr)}}{3600 \text{ s/hr}} - \text{Blank Correct Uptake (g)}}{\text{Dry Weight of Sample (g)}}$$

Initial Effective Uptake Rate at 200 cm ("IEUR")

IEUR (g/g/hr)=CSAC at 200 cm (g/g)
Sample Time at 200 cm (s)

Reporting

A minimum of two measurements should be taken for each sample and the uptake averaged at each height to calculate Capillary Sorption Absorbent Capacity (CSAC) for a given absorbent member or a given high surface area material.

With these data, the respective values can be calculated:

The Capillary Sorption Desorption Height at which the material has released x % of its capacity at 0 cm (i.e. of CSAC 0), (CSDH x) expressed in cm;

The Capillary Sorption Absorption Height at which the material has absorbed y % of its capacity at 0 cm (i.e. of CSAC 0), (CSAH y) expressed in cm;

The Capillary Sorption Absorbent Capacity at a certain height z (CSAC z) expressed in units of g {of fluid}/g {of material}; especially at the height zero (CSAC 0), and at heights of 35 cm, 40 cm, etc The Capillary Sorption Absorption Efficiency at a certain height z (CSAE z) expressed in %, which is the ratio of the values for CSAC 0 and CSAC z.

If two materials are combined (such as the first being used as acquisition/distribution material, and the second being used as liquid storage material), the CSAC value (and hence the respective CSAE value) of the second material can be determined for the CSDH x value of the first material.

Reversible Expansion Test

The intention of this test is to measure the expansion of a liquid handling member and the subsequent contraction of the liquid handling member over a series of liquid acquisition and release cycles. This test this suitable for liquid handling members according to the present invention. This test maybe equivalently applied to devices for handling body liquids according to the present invention.

The test specimen is a liquid handling member according to the present invention. The liquid handling member should be configured to resemble as closely as possible its in use configuration. If the liquid handling member is part of the device for handling body liquids, those parts of the device which do not contribute to the performance of the liquid handling member may be removed prior to testing the liquid handling member. It is, however, also possible to test a device for handling body liquids in its entirety.

At the beginning of the test, the total absorbent capacity of the specimen is determined via the demand absorbency test defined herein. The specimen which is now filled with liquid up to its total absorbent capacity is now placed on the glass frit of the capillary sorption test defined herein which has been set at 0 cm hydrohead.

The experimental set up for this test comprises the set up for the capillary sorption test defined herein in combination with a volume measurement device which is installed such that it is capable of measuring the dimensions of the specimen when the specimen is placed on the glass frit of the capillary sorption experimental set up.

For the purpose of this test, a Cartesian coordinate system is defined as follows. The z-direction is direction perpendicular to the upper major surface of the glass frit also termed caliper direction about. Accordingly, x-, and y-direction are parallel to the upper major surface of the glass frit. The x-direction is defined by the direction of most efficient liquid transportation within the test specimen. For example, if the test specimen has a first region for liquid acquisition and the second region for liquid discharge or storage the x-direction would point from the first region to the second region.

For example, the volume measurement device may consist of a caliper (z-direction) measurement device, in combination with two devices which measure the expansion of the test specimen in the two dimensions (x-, and y-direction) parallel to the surface of the glass frit. Since the two major surfaces of the glass frit in the capillary sorption experimental setup are oriented horizontally, the caliper measurement device in this test measures the vertical expansion of the test specimen whereas the other two measurement devices measure the horizontal expansion of the test specimen. If, for example, the test specimen is substantially rectangular simple mechanic devices for manual determination of length may be used to determine the dimensions of the test specimen. If the geometry of the test specimen is more complex, contraction and expansion of the test specimen may be recorded for example on video tape which allows for exact analysis of expansion and contraction of the test specimen during the test. Suitable methods for the determination of each of the dimensions are well known in the art. If such method requires that the test specimen is put under a confining pressure, the confining pressure should be chosen low enough such that the respective dimension of the test specimen remains substantially unchanged. Furthermore, it is important that a dimension of the test specimen is measured over a surface area which is at least 20 percent of the respective surface area of the test specimen such that the measurement is representative of the dimension.

During the first step of this test, the total absorbent capacity of the test specimen is determined via the demand absorbency test defined herein. The test specimen which is now fit with liquid up to its total absorbent capacity is now placed on the glass frit of the capillary sorption test defined herein which has been set at 0 cm hydrohead. On the glass frit, the test specimen is oriented such that its region which is intended for liquid acquisition is facing towards the upper surface of the glass frit.

During the second step of this test, the capillary suction is continuously increased until half of the liquid initially stored in the liquid handling member is removed from the liquid handling member or device respectively. At the beginning of this step and at the end of this step, the dimensions of the liquid handling member or the device are recorded. The contraction factor for each dimension is determined by dividing the respective dimension of the test specimen at the end of this test phase by its respective dimension at the beginning of this test phase. Accordingly, the value of each contraction factor will be between 0 and 1. The volume contraction factor is determined by dividing the volume at the end of this step by the volume at the beginning of this step. For a substantially rectangular test specimen for example, the volume may be obtained by multiplying the x-, y-, and the z-dimension of the test specimen.

During the third step of this test the capillary suction is decreased to zero pressure such that the test specimen will take up liquid again until the specimen is filled up to its total capacity. At the beginning of this test phase and at the end of this test phase, the dimensions of the liquid handling member or the device are recorded. The expansion factor for each dimension is determined by dividing the respective dimension of the test specimen at the end of this test phase by its respective dimension at the beginning of this test phase. Often, the value of each expansion factor will be at least 1. The volume expansion factor is determined by dividing the volume at the end of this test phase by the volume at the beginning of this test phase. In addition, the liquid capacity at the end of the cycle is divided by the total absorbent capacity of the test specimen as determined by the demand absorbency test prior to this test to obtain the capacity decrease factor.

The above measurement cycle of second step and third step may be repeated in order to examine the longtime behavior of the test specimen. The respective contraction factors, expansion factors, and capacity decrease factors are then denoted together with the number of their respective test cycle.

What is claimed is:

1. A liquid handling member characterized in that said liquid handling member has a volume contraction factor of less than 0.8 after the first test cycle and a volume expansion factor of at least 1.25 after the first test cycle according to the reversible expansion test defined herein and said liquid handling member has a 80% absorption time of less than 2 seconds according to the Demand Absorbency Test defined herein.

2. A liquid handling member according to claim 1, wherein said liquid handling member has a volume contraction factor of at least 0.9 after the second test cycle according to the reversible expansion test defined herein.

3. A liquid handling member according to claim 1, wherein said liquid handling member has a volume expansion factor of at least 1.11 after the second test cycle according to the reversible expansion test defined herein.

4. A liquid handling member according to claim 1, wherein said liquid handling member has a capacity decrease factor of at least 0.8 after the first test cycle of the reversible expansion test defined herein.

5. A liquid handling member according to claim 1, wherein said liquid handling member has a capacity decrease factor of at least 0.7 after the second test cycle of the reversible expansion test defined herein.

6. A liquid handling member according to claim 1, wherein said liquid handling member has a absorbent capacity of at least 80 percent of an average gush volume for an intended use of said liquid handling member according to the demand absorbency test defined herein.

7. A liquid handling member according to claim 1, wherein said liquid handling member has a medium desorption pressure of less than 20 cm according to the capillary sorption test defined herein.

8. A liquid handling member according to claim 1, wherein said liquid handling member has a trans-planar permeability of at least 10 Darcy according to the Permeability Test defined herein.

9. A liquid handling member according to claim 1, wherein said liquid handling member is substantially geometrically saturated with liquid before the intended use of the liquid handling member.

10. The liquid handling member according to claim 9, where in said liquid handling member is substantially geometrically saturated with free liquid.

11. A device for managing body liquids comprising a liquid handling member according to claim 1.

12. A device for handling body liquids according to claim 11, wherein set liquid handling member has a absorbent capacity of at least 20 percent of the total design capacity of said device for handling body liquids according to the demand absorbency test defined herein.

13. A device for handling body liquids according to claim 11, wherein said device is a disposable absorbent article.

14. A device for handling body liquids according to claim 13, wherein said device is a disposable diaper.

15. A device for handling body liquids according to claim 14, wherein said liquid handling member has a capacity of at least 60 ml according to the Demand Absorbency Test defined herein.

* * * * *

UNITED STATES PATENT AND TRADEMARK OFFICE
CERTIFICATE OF CORRECTION

PATENT NO. : 6,545,194 B1
DATED : April 8, 2003
INVENTOR(S) : Schmidt et al.

It is certified that error appears in the above-identified patent and that said Letters Patent is hereby corrected as shown below:

Column 4,
Line 65, please delete "CM1841 MQ" and insert therefore -- CM1841MQ --.

Column 9,
Line 14, please delete "indus- " and insert therefore -- Indus - -- .
Line 47, please delete "Coming" and insert therefore -- Corning --.

Column 10,
Line 19, please delete "Teflone" and insert therefore -- Teflon --.

Column 15,
Line 27, please delete "+" after "31".

Column 18,
Line 15, please delete "- " after "measuring".

Signed and Sealed this

Twenty-second Day of June, 2004

JON W. DUDAS
*Acting Director of the United States Patent and Trademark Office*